United States Patent [19]

Biselli et al.

[11] Patent Number: 5,130,026
[45] Date of Patent: Jul. 14, 1992

[54] PROCESS AND APPARATUS FOR REMOVING AMMONIUM FROM AQUEOUS LIQUIDS

[75] Inventors: Manfred Biselli, Juelich; Joerg Thoemmes, Bonn; Christian Wandrey, Juelich, all of Fed. Rep. of Germany

[73] Assignee: Forschungszentrum Juelich GmbH, Juelich, Fed. Rep. of Germany

[21] Appl. No.: 705,655

[22] Filed: May 24, 1991

[30] Foreign Application Priority Data

May 25, 1990 [DE] Fed. Rep. of Germany ....... 4016971

[51] Int. Cl.$^5$ .............................................. B01D 15/04
[52] U.S. Cl. ................... 210/638; 210/639; 210/741; 210/743; 210/195.2; 210/321.75; 55/70; 55/54; 55/55
[58] Field of Search ............... 210/638, 639, 643, 641, 210/648, 670, 651, 681, 195.2, 321.75, 741, 743; 55/54, 55, 70

[56] References Cited

U.S. PATENT DOCUMENTS

| | | | |
|---|---|---|---|
| 3,842,000 | 10/1974 | Dawson | 210/648 |
| 4,547,293 | 10/1985 | King et al. | 210/638 |
| 4,591,439 | 5/1986 | Grot | 210/638 |
| 4,647,380 | 3/1987 | Dasgupta | 210/638 |
| 4,650,587 | 3/1987 | Polak et al. | 210/638 |
| 4,768,250 | 7/1988 | Laciak et al. | |

OTHER PUBLICATIONS

Rautenbach et al., "Aufarbeitung Ammoniak enthaltender Abwässer—Verfahrens- und Kostenvergleich", Chem.-Ing.-Tech. 60, vol. 1, 1988, pp. 23-31.
Abstracts, vol. 108, 1988, 108:113717f, Takada et al., "Studies on appl. of substituted polyacetylene IV. Appl. of substituted polyacetylenes to semipermeable membranes. The possibility of loose RO membrane."
Chemical Abstracts, vol. 98, 1983, 98:145885a, "Ion separation by combination of permeation through ion-exchanging membrane and chelation," p. 42.
Abstracts, vol. 98, 1983, 98:199358z, "Amphoteric electrolyte membranes prepared by alternating copolymerization", p. 41.

Primary Examiner—W. Gary Jones
Assistant Examiner—Ana Fortuna
Attorney, Agent, or Firm—Foley & Lardner

[57] ABSTRACT

A process for the removal of ammonium from aqueous liquids, especially from fermentation broths, is disclosed. The process uses a cation exchanger membrane which separates a liquid on a donor side that is to be depleted of $NH_4^+$ from a solution on an acceptor side whose pH is higher than on the donor side. Because of the equilibrium $$NH_4^+ \rightleftharpoons NH_3 + H^+$$

there is on the acceptor side increased formation of $NH_3$. This is continuously removed, in particular by reducing the pressure and/or passing through inert gas, or by selective transport through another microporous membrane into an acid protonation solution, so that a $NH_4^+$ concentration gradient is maintained across the membrane. A similar content, apart from the ammonium concentration, of concomitant cations on the donor and acceptor side and/or a high ratio of the solution volumes on the donor side and the acceptor side ensures that the solution on the donor side to be depleted of $NH_4^+$, does not lose concomitant ions. A suitable apparatus comprises a flow section which can be coupled into a bypass and has a cation exchanger limiting membrane which is simultaneously a limiting wall of an acceptor chamber. The acceptor chamber may contain devices for pH control and $NH_3$ removal or these may be contained in a flow section.

13 Claims, 6 Drawing Sheets

PROCESS AND APPARATUS FOR REMOVING AMMONIUM FROM AQUEOUS LIQUIDS

BACKGROUND OF THE INVENTION

The present invention relates to a process for the removal of ammonium from cation-containing aqueous liquids, especially fermentation broths, through a transport membrane and selective elimination on the acceptor side, and to an apparatus suitable therefor.

In many fermentation processes, ammonium ions inhibit growth and productivity. This is particularly important in the cultivation of mammalian cells. It is therefore expedient to reduce the ammonium concentration in fermentation processes in order to achieve higher biomass concentrations and higher productivities.

A process for reducing ammonium concentration in such liquids has already been developed and is based on the equilibrium between ammonium and ammonia in such culture liquids, the content of the latter therein being a few percent (Wissenschaftlicher Ergebnisbericht der GBF 1985, pages 20–22). In this process, the ammonia is removed through a porous membrane (polypropylene tube) by diffusion and is taken up by an acid medium on the secondary side of the membrane, and the ammonium ions formed thereby are removed by ion exchange. There is also a report on this procedure by Soeters et al in *Advances in Ammonia Metabolism and Hepatic Encephalopathy* 69: 534–42 (1988).

Busse et al describe, in *J. Hepatology* 1 to Vol. 4, p. 10 (1987), the removal of ammonium by means of a lipid hollow-fiber membrane reactor. In this case, ammonium ions on the donor side diffuse as ammonia through a lipophilic hollow-fiber membrane and are converted on the acceptor side either by a pH shift as above or enzymatically with α-ketoglutarate and NADH into glutamic acid, and thus removed from the transport equilibrium.

T. Pultar et al, DECHEMA BIOTECHNOLOGY CONFERENCES 3—VCH VERLAGSGESELLSCHAFT 1989, pp. 567–71, mention the removal of ammonium ions from culture liquids by adduct formation between ammonium ions and calcium phosphate, but this is described as imperfect. For this reason, the diffusion outlined above, of ammonia through a porous membrane whose acceptor side is flushed with acid solution, is said to be favored.

Another process for reducing the ammonium concentration is described by M. Iio et al in R. Murakami (eds.) GROWTH AND DIFFERENTIATION OF CELLS IN DEFINED ENVIRONMENT, Springer-Verlag, New York 1984, pp. 437–42. The ammonium is absorbed by a suspension of hydrothermally-generated aluminum silicate ZCP-50 in a dialysis tube.

T. E. Hassell et al mention in Spier and Griffiths (eds.) MODERN APPROACHES TO ANIMAL CELL TECHNOLOGY, Butterworths, London 1987, p. 245–63, the reduction in the level of ammonium by replacing glutamine by glutamate or 2-oxo-glutarate.

The above mentioned techniques for reducing the ammonium concentration in cell culture liquids do not appear to be entirely satisfactory. In particular the removal by diffusion of ammonia, which is substantially favored, may give rise to problems over lengthy periods and as a consequence of a change or blockage in the pore structure. Furthermore, the transport rates through the membrane which can be achieved are low, so that very large membrane areas are required.

SUMMARY OF THE INVENTION

It is therefore an object of the invention to produce an efficient process for reducing the ammonium content in aqueous liquids, especially cell culture liquids, which can be carried out without problems.

These and other objects according to the invention are provided by a process for the removal of ammonium from a cation-containing aqueous liquid by passage through a transport membrane and selective elimination on the acceptor side, comprising the steps of providing a cation exchanger membrane having an acceptor side and a donor side; establishing a pH on the acceptor side which is higher than that on the donor side such that there is a $NH_4^+$ concentration gradient across the membrane by reason of an equilibrium between ammonium and ammonia; removing ammonia from a solution on the acceptor side; and preventing cations other than $NH_4^+$ from being removed from the solution on the donor side, that means their concentrations should not decrease below values necessary in the donor side solution. When removing ammonium ions from a fermentation broth care should be taken not to lower the concentrations of the essential cations below cell growth promoting values.

The invention also provides an apparatus for removing ammonium from a cation-containing aqueous liquid comprising a cation exchanger limiting membrane which separates an ammonium-containing donor stream from an acceptor stream; means for establishing and maintaining a pH in the acceptor stream which is higher than that in the donor stream such that there is a $NH_4^+$ concentration gradient across the membrane by reason of an equilibrium between ammonium and ammonia; and means for removing ammonium from the acceptor stream.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

The process according to the invention uses a cation exchanger membrane and provides a pH on the acceptor side which is higher than that on the donor side so that there is a $NH_4^+$ concentration gradient across the membrane resulting from the equilibrium between ammonium and ammonia. Ammonia is removed from the solution on the acceptor side. The content of cations other than $NH_4^+$ in the solution on the acceptor side should correspond to that in the solution on the donor side. Alternatively, the volume of the acceptor side solution involved in the exchange through the membrane should amount to no more than 10% of the total liquid volume on the donor side.

Figure 6:
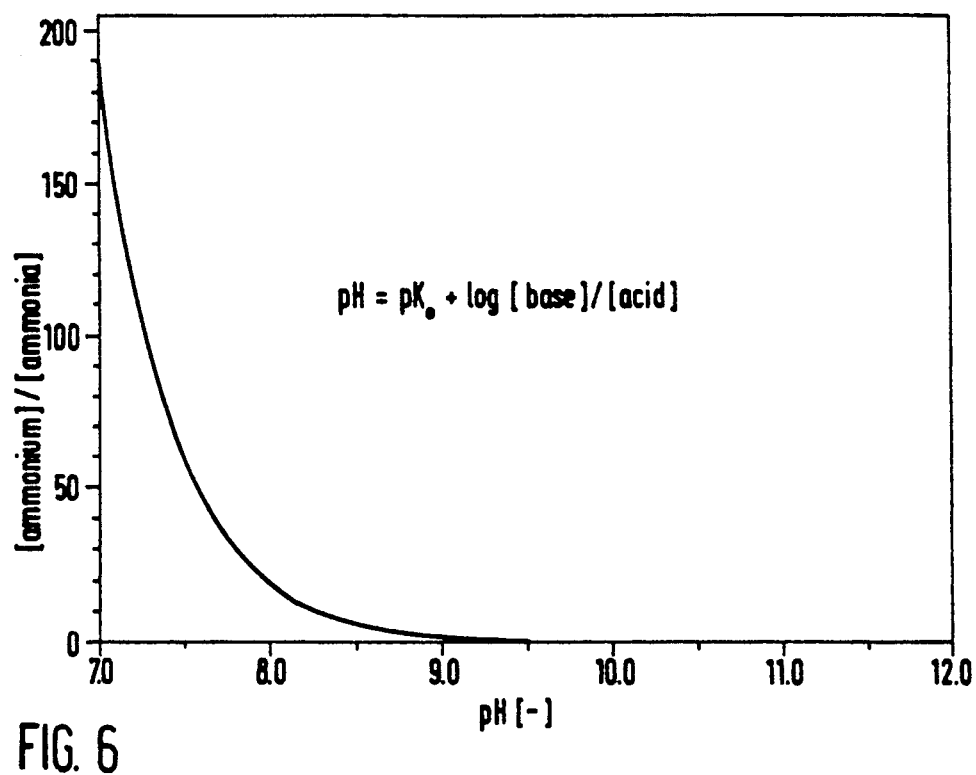
FIGS. 6 through 8 are plots illustrating the principle of $NH_4^+$ removal according to the invention.
Figure 8:
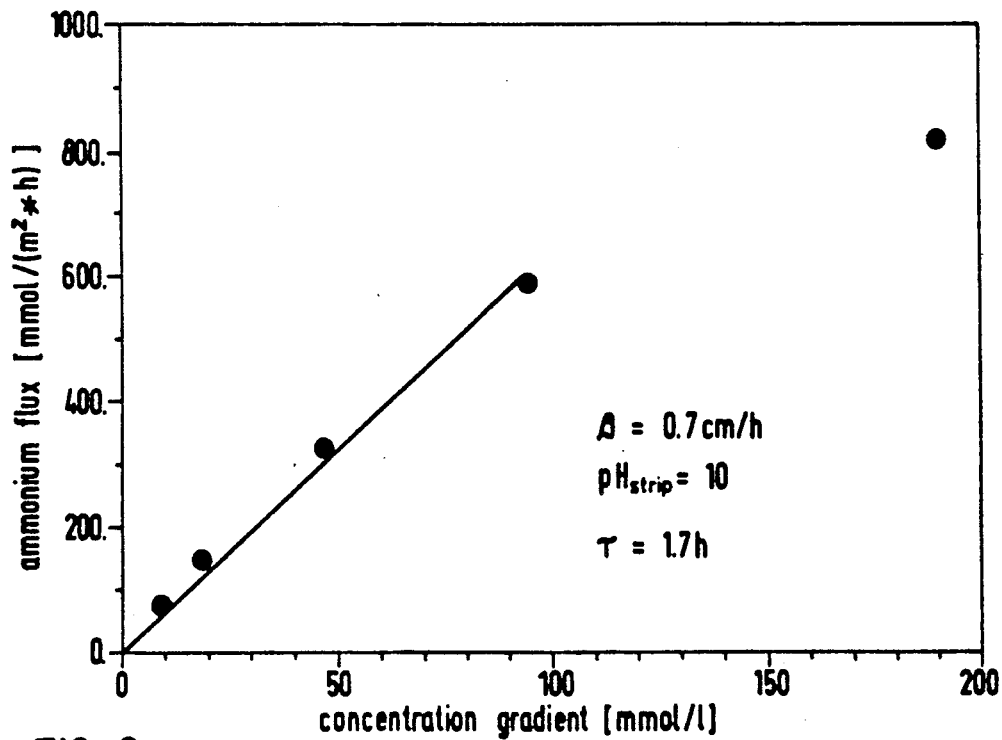
Figure 7:
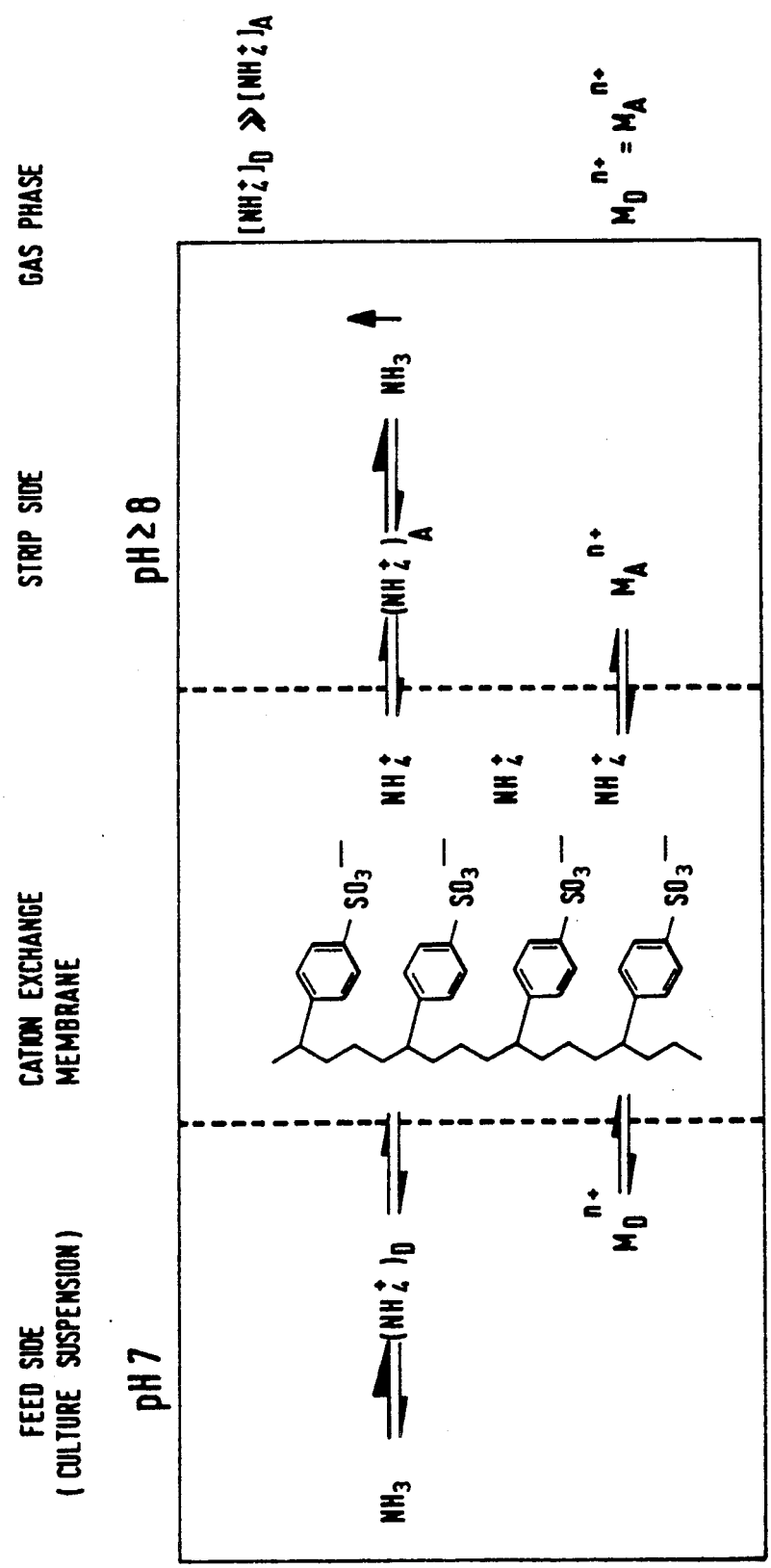

Thus, according to the invention, the selectivity of ammonium removal is achieved, not as previously by $NH_3$ diffusion through a hydrophobic membrane, but by equalization of the cation contents on the donor and acceptor side and by a steep $NH_4^+$ drop toward the acceptor side. This promotes the transport of $N_4^+$ through a cation exchanger membrane. This process is based on the much higher $NH_4^+$ concentration compared with the $NH_3$ concentration (see FIG. 6) in biological systems with pH values around the neutral point. The concentration difference acts as a "motor" for an enhanced ammonium transport toward the acceptor side, where a higher pH ensures a low $NH_4^+$ concentration because of equilibrium-related deprotonation to $NH_3$. This diffusion promoting $NH_4^+$ reduction on the acceptor side is additionally enhanced by removal of $NH_3$ from the system on the acceptor side (see FIG. 7). The increase in the $NH_4^+0$ transport rate as the concentration gradient across the membrane increases is shown in FIG. 8.

Usually the liquids of the donor side will be pH-regulated liquids as e.g. fermentation broths having pH-values in the range from slightly acid to neutral. The pH-values of the acceptor side solution is continuously controlled at values which are conveniently at least one pH-unit higher than that of the donor side liquid. Corresponding to the transported amount of $NH_4^+$ ions a pH-regulans, especially NaOH, is supplied to the acceptor side solution. Usually the acceptor side pH will be controlled by means of a pH-stat.

The removal of ammonia from the solution on the acceptor side can be effected, inter alia, by reducing the pressure or by passing through a gas (variant A), but the method known per se of diffusion of ammonia through a porous membrane with secondary side protonation to ammonium is particularly used (variant B). Overall, the steps which take place are as follows:

Variant A

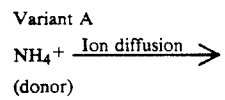
(donor)

Figure 1:
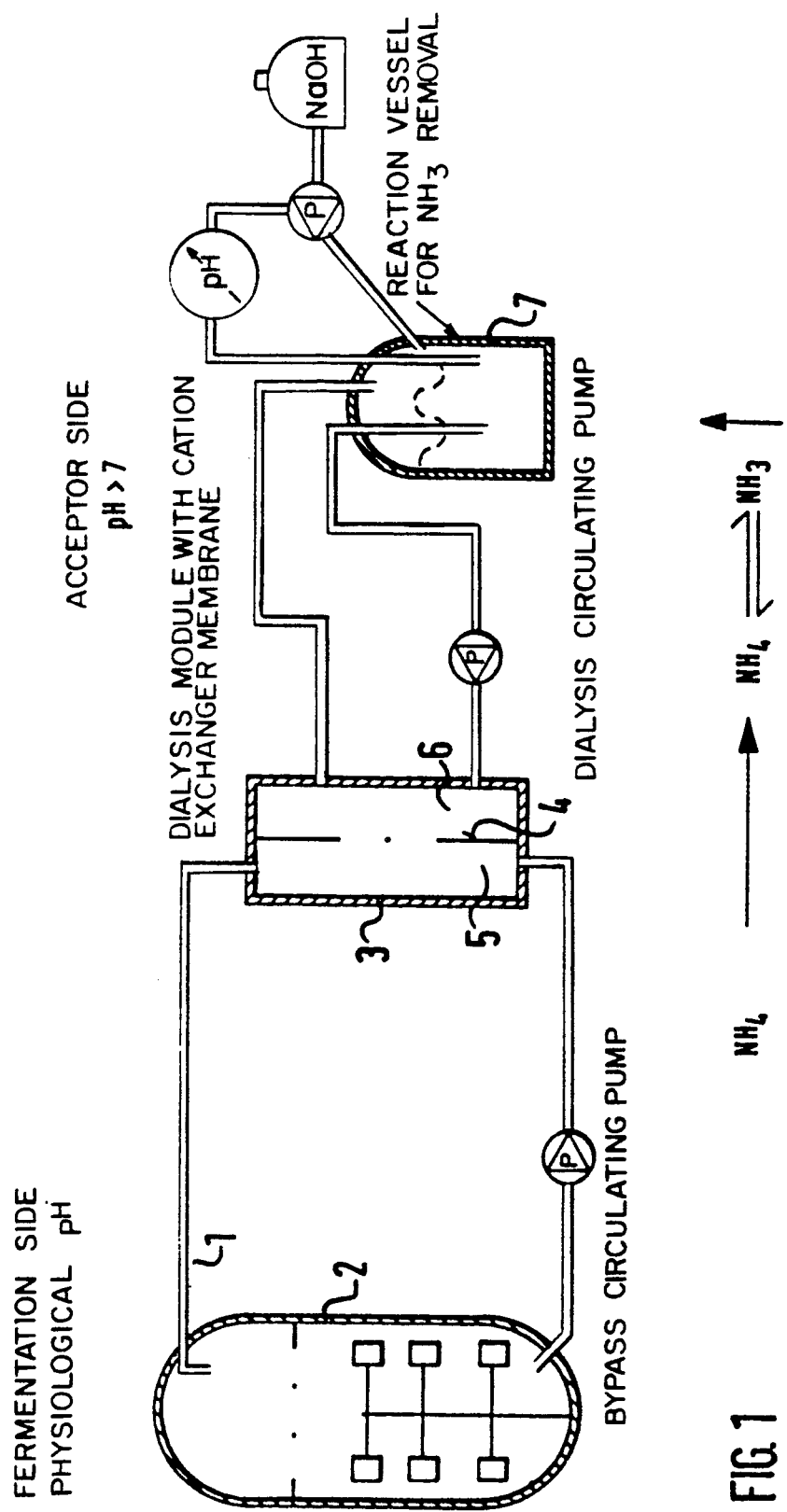
FIGS. 1 and 2 are diagrams of an arrangement according to the invention.

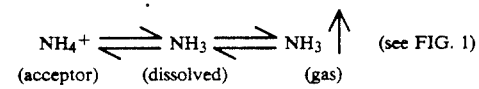 (see FIG. 1)

Variant B

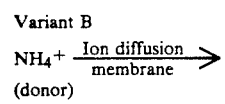
(donor)

Figure 2:
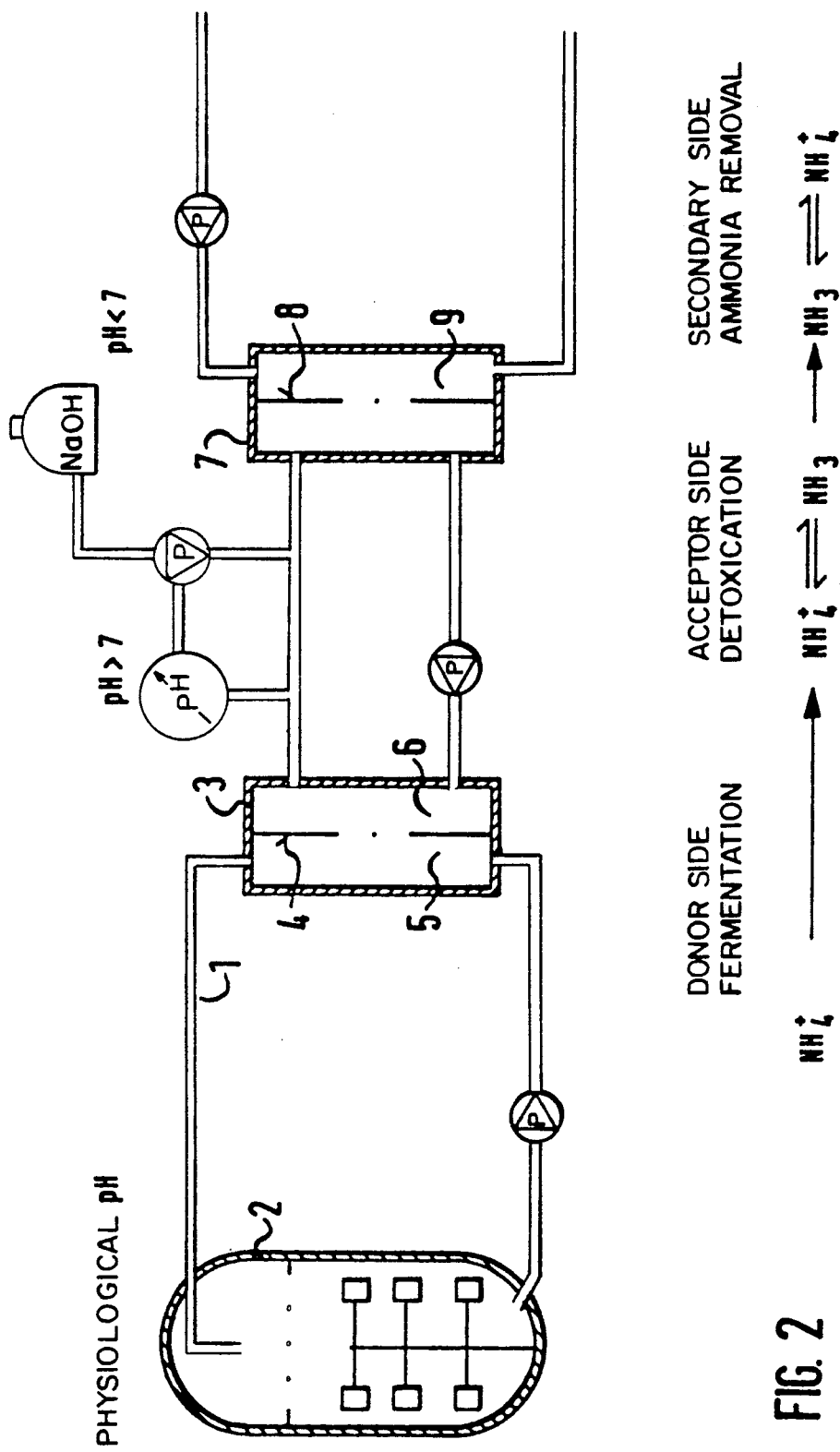

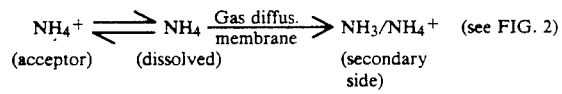 (see FIG. 2)

It is possible in principle to use a stationary acceptor solution, from which the ammonia is removed continuously, especially by reducing the pressure or passing through an inert gas, but it is preferable to pass a stream of acceptor solution continuously over the membrane on the acceptor side and then to an arrangement for removing $NH_3$.

A real fermentation broth contains not only ammonia but also many other cations whose transport through the limiting cation exchanger membrane takes place to more or less the same extent as ammonium. Moreover, smaller ions pass through the membrane particularly rapidly because of their greater mobility. Various procedures are possible to prevent noticeable losses of cations and thus a reduction in concentration thereof in the donor solution. In order to prevent this, it is possible to use as acceptor solution a fermentation medium which is cell-free, but which is provided with all the cationic ingredients necessary for growth and which contains all necessary cations in the same concentration as the donor side solution, but at increased pH. In this way, dilution on the donor side is avoided.

The cations essential for the growth of the biomass in the fermentation or donor solution are thus located on both sides in equilibrium concentration, and no migration out of the fermentation broth takes place. However, because there is no biological system in the acceptor solution, there is no production of ammonium so that the concentration gradient necessary for removing the ammonium from the donor solution is present. This acceptor solution can continuously pass the membrane and thus absorb as ammonia, by reason of the pH shift, the ammonium which is continuously formed on the donor side and passes through the membrane.

As an alternative to or in addition to maintaining equal concentration of cations other than $NH_4^+$ on both sides of the membrane, the acceptor solution can have a small volume in relation to the donor solution and not be continuously replaced. In this way, because of the low volume, an equilibrium concentration between donor and acceptor solution is rapidly set up, the value of which is close to the original value of the donor solution. Few cations are withdrawn from the donor solution to set up the equilibrium. The ammonium concentration then likewise rapidly reaches an equilibrium value which is determined by the solubility of the ammonia produced by deprotonation in the acceptor solution. The ammonia must therefore be removed from the acceptor solution in order to maintain the concentration gradient necessary for transport.

It is possible for this purpose to pass helium through the acceptor solution in order to degas the latter. Also suitable for this purpose is a slight reduction in pressure. It is important to remove the dissolved ammonia continuously from the acceptor solution into the gas phase over the solution in order to allow continuous transport of ammonium ions through the membrane along the concentration gradient from the donor to the acceptor solution. This gradient then persists as a result of the further reaction of the ammonium to the ammonia in the alkaline acceptor solution.

However, ammonia is particularly expediently removed by diffusion through a porous membrane, as already mentioned above. The membrane can be a barrier for a stationary acceptor solution, but it is preferable to provide a circulation of acceptor solution, which passes both over the acceptor side of the cation exchanger membrane and over the primary side of the porous $NH_3$ diffusion membrane. The secondary side of the NH₃ diffusion membrane is flushed by a stream of acid protonation solution, which can be discarded without difficulty.

An apparatus suitable for carrying out the process according to the invention essentially comprises a flow section which can be coupled into a bypass and has a cation exchanger limiting membrane which is simultaneously a limiting wall of an acceptor chamber which either directly contains devices for pH control and $NH_4^+$ removal or is part of a flow section containing such devices.

EXAMPLE

The dialysis apparatus shown in FIG. 1 was used. Dialysis module 3 includes cation exchanger membrane 4, e.g., polystyrenesulfonate "Permion 4010" supplied by SERVA (membrane area: 13.4 cm²) which separates donor stream 5 from acceptor stream 6. Module 3 is inserted into bypass 1 of fermenter 2. Acceptor stream 6 is circulated through reaction vessel 7 in which the ammonia is driven out as gaseous $NH_3$.

Figure 3:
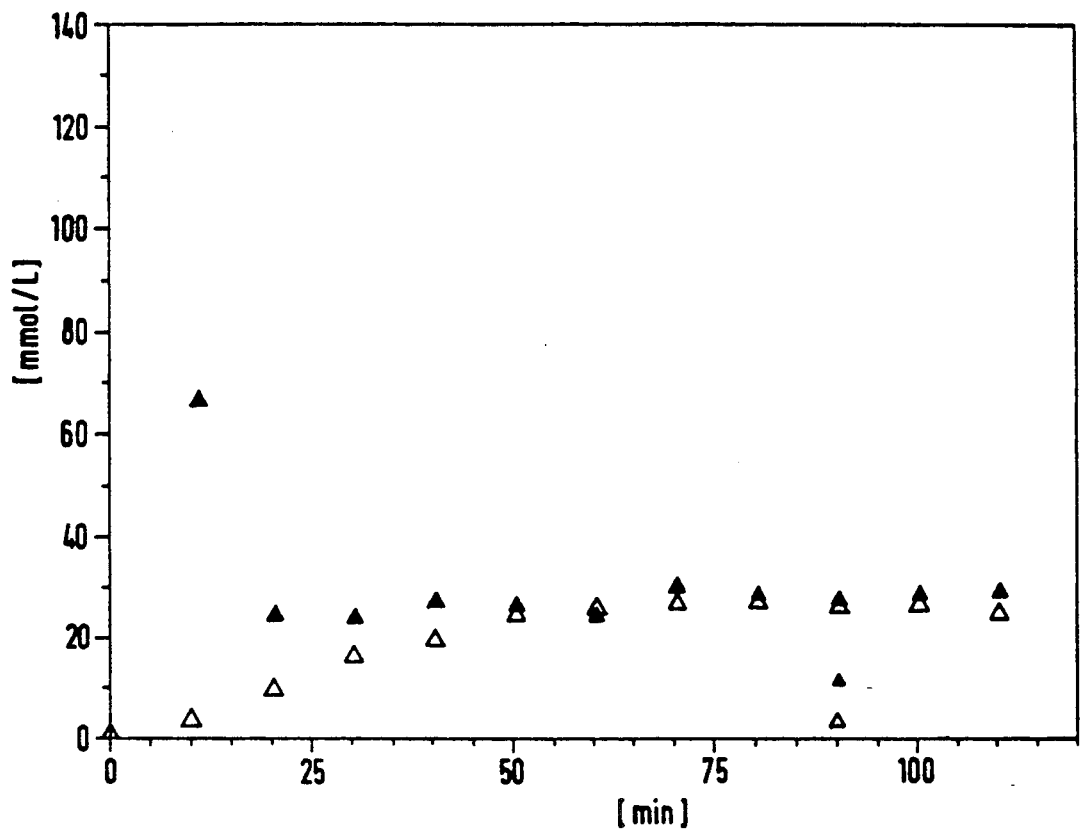
FIG. 3 is a graph of the ammonium concentration in donor and acceptor solution on use of the process according to the invention as a function of time.

In a model experiment without biomass, an aqueous solution composed of 100 mM HEPES buffer (pH 7), 100 mM NaCl and 100 mM ammonium chloride was dialyzed in this apparatus on the donor side against a solution of 100 mM HEPES buffer (pH 8) and 100 mM NaCl on the acceptor side. The degassing and thus the removal of the ammonia produced by deprotonation was effected by bubbling a moderate stream of helium through the acceptor solution. Samples from the donor and acceptor sides were investigated at 10 minute intervals for their ammonium content (see FIG. 3). There was found to be a linear decrease in the ammonium concentration on the donor side to an equilibrium value. The rate of substance transfer is calculated from the fall in ammonium concentration on the donor side. It was 5.5 mol/hm² membrane area in the present example.

Figure 4:
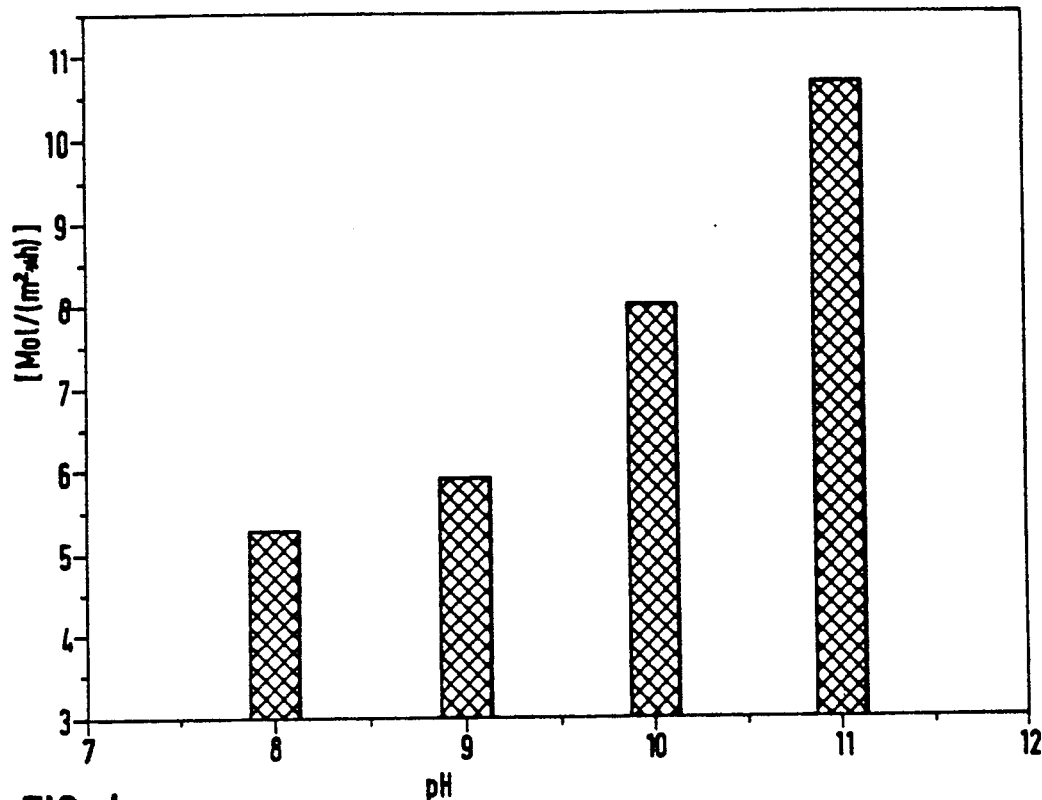
FIG. 4 is a diagram of the rates of transfer of ammonium ions through the cation exchanger membrane as a function of the pH on the acceptor side.
Figure 5:
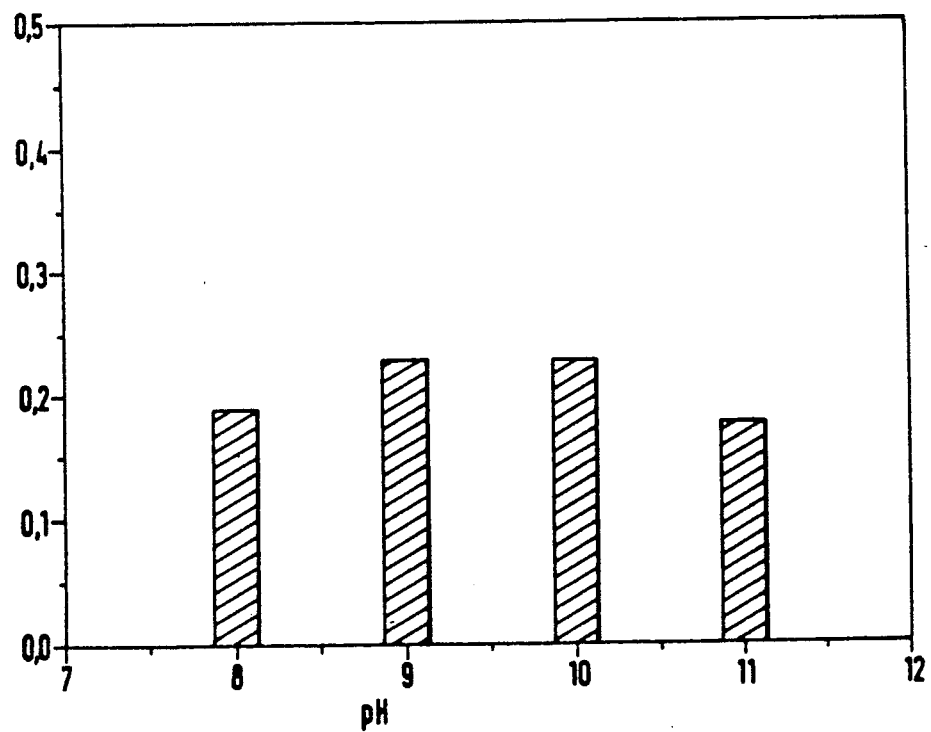
FIG. 5 is a diagram of the proportion of ammonium remaining, expressed as equilibrium value divided by initial concentration, on the donor side as a function of the acceptor pH.

Investigation of the rate of substance transfer as a function of the pH of the acceptor solution revealed an increase as the pH increased (see FIG. 4). The equilibrium concentration of ammonium which is set up on the donor side can be expressed as the proportion remaining (equilibrium concentration:initial concentration). It is evidently independent of the pH of the acceptor solution (see FIG. 5) and is determined only by the solubility of ammonia in the acceptor solution.

FIG. 2 shows a preferred variant of the dialysis apparatus from FIG 1. Dialysis module 3 includes cation exchanger membrane 4, e.g., polystyrenesulfonate "Permion 4010" from SERVA (membrane area 13.4 cm²), which is inserted into bypass 1 of fermenter 2 to separate donor stream 5 from acceptor stream 6. Acceptor stream 6 is circulated through second dialysis module 7 which contains microporous membrane 8 as boundary to a secondary stream. This acid secondary stream 9 is continuously passed over microporous membrane 8 and, after passage, is expediently discarded.

The laboratory arrangement depicted diagrammatically in two variants was implemented and operated as follows:

(1) Dialysis module

The dialysis module is designed to receive a flat membrane. The latter is placed between the two halves of the module, and screwing together the halves of the module brings about, via silicone seals, a seal between the membrane and the halves of the module. Each half of the module has two connections for inflow and outflow of liquids. The liquid stream is passed tangentially with a small cross-section past the membrane in order to achieve a high rate of overflow. The required area of overflow is obtained by guiding the stream in a meandering manner. The material is preferably, for reasons of autoclavability, stainless steel, which must have minimal roughness on the areas in contact with the process liquid to prevent mechanical damage to the biomass passing through the module. The size of the module depends on the membrane area needed to remove an appropriate amount of ammonium. This is calculated from the substance transfer data.

(2) Donor circulation

The donor circulation is attached as a bypass around the fermentation system, i.e., the fermentation liquid circulates in the donor circulation and, after passing through the module, is returned to the fermentation system. A tubing pump of low shear stress and with autoclavable pump tubing should be used as the circulating pump in order to take account of the direct connection to the biological system.

(3) Acceptor circulation

The circulation is maintained at a pH that is at least one pH unit higher than the fermentation and contains an apparatus for removing $NH_3$ from the acceptor solution. This apparatus can, on the one hand, comprise a stirred, pressure-resistant reaction vessel which can be thermostated. The $NH_3$ is removed either by passing in sterile-filtered helium or by reducing the pressure, likewise under sterile conditions. On the other hand, the apparatus can comprise a second dialysis module such as either a hollow-fiber or flat membrane, which separates the acceptor solution by means of a microporous membrane from a secondary stream. The secondary stream is set at a pH below 7 in order to ensure protonation of the $NH_3$ and thus a continuous ammonia gradient across the porous membrane.

What is claimed is:

1. A process for the removal of ammonium from a cation-containing aqueous liquid, comprising the steps of:
   providing a cation exchanger membrane in contact with said liquid as a donor side liquid, said membrane being on its back side in contact with an acceptor solution;
   establishing a pH on the acceptor side which is higher than that on the donor side such that there is a $NH_4^+$ concentration gradient across the membrane by reason of an equilibrium between ammonium and ammonia;
   removing ammonia from a solution on the acceptor side; and
   preventing the concentration of cations other than $NH_4^+$ from being reduced in the solution on the donor side.

2. The process as claimed in claim 1, wherein reduction in concentration of cations other than $NH_4^+$ is prevented by maintaining equal concentrations of the other cations on both sides of the membrane.

3. The process claimed in claim 1, wherein reduction in concentration of cations other than $NH_4^+$ is prevented by maintaining an exchange volume that is no more than 10% of the total liquid volume on the donor side.

4. The process as claimed in claim 1, wherein the removal of the ammonia from the solution on the acceptor side is effected by passing an inert gas through the solution.

5. The process as claimed in claim 1, wherein the removal of the ammonia from the solution on the acceptor side is effected by selective transport through a microporous hydrophobic membrane into an acid protonation solution.

6. The process as claimed in claim 1, wherein the removal of the ammonia from the solution on the acceptor side is effected by reducing the pressure.

7. The process as claimed in claim 1, wherein the liquid on the donor side is derived directly from a pH-static fermentation system.

8. The process as claimed in claim 1, wherein an increase in pH by at least one pH unit is provided on the acceptor side relative to the donor side.

9. The process as claimed in claim 1, wherein a cell-free culture liquid is provided on the acceptor side.

10. The process as claimed in claim 1, wherein a liquid stream of low layer thickness is provided on the acceptor side.

11. The process as claimed om claim 1, wherein the exchange volume ratio through the membrane between the donor and acceptor side is greater than or equal to 20.

12. The process as claimed in claim 1, wherein said donor side liquid that is in contact with the donor side of the cation exchanger membrane is a culture liquid that is continuously passed through a bypass line that goes to the donor side of the cation exchanger membrane.

13. An apparatus for removing ammonium from a cation containing aqueous liquid comprising:
 a cation exchanger limiting membrane which separates an ammonium-containing donor stream from an acceptor stream;
 means for establishing and maintaining a pH in the acceptor stream which is higher than that in the donor stream such that there is a $NH_4^+$ concentration gradient across the membrane by reason of an equilibrium between ammonium and ammonia; and
 means for removing ammonia from the acceptor stream.

* * * * *